(12) United States Patent
Cappa

(10) Patent No.: US 9,469,979 B1
(45) Date of Patent: Oct. 18, 2016

(54) DEODORIZING SINK SYSTEM

(71) Applicant: Jonathan E. Cappa, Palm Harbor, FL (US)

(72) Inventor: Jonathan E. Cappa, Palm Harbor, FL (US)

(*) Notice: Subject to any disclaimer, the term of this patent is extended or adjusted under 35 U.S.C. 154(b) by 0 days.

(21) Appl. No.: 14/788,885

(22) Filed: Jul. 1, 2015

Related U.S. Application Data

(60) Provisional application No. 62/020,477, filed on Jul. 3, 2014.

(51) Int. Cl.
| | | |
|---|---|---|
| *E03D 9/02* | (2006.01) | |
| *E03C 1/18* | (2006.01) | |
| *A61L 9/01* | (2006.01) | |

(52) U.S. Cl.
CPC ... *E03C 1/18* (2013.01); *A61L 9/01* (2013.01)

(58) Field of Classification Search
CPC .... E03C 1/126; E03C 1/2665; E03D 13/005
USPC ............ 210/163, 164; 241/46.013; 4/222, 4/222.1, 231, 288–294, 309, 652, 655, 4/661, 695, DIG. 4
See application file for complete search history.

(56) References Cited

U.S. PATENT DOCUMENTS

| | | | | |
|---|---|---|---|---|
| 3,760,429 | A * | 9/1973 | Brownstein | E03D 13/005 4/222 |
| 5,165,119 | A * | 11/1992 | Yamato | E03D 9/032 4/222.1 |
| 7,458,108 | B2 * | 12/2008 | Wolf | A47K 1/14 4/222 |
| 8,136,173 | B2 * | 3/2012 | Knox | E03C 1/126 4/255.08 |
| 8,409,433 | B2 * | 4/2013 | Worth | C02F 1/68 210/163 |
| 2011/0289665 | A1 * | 12/2011 | Lees | E03D 13/00 4/222 |

FOREIGN PATENT DOCUMENTS

GB       2473055       *   3/2011   ............ E03D 13/00

* cited by examiner

*Primary Examiner* — Paul R Durand
*Assistant Examiner* — Nicholas Ros

(57) ABSTRACT

A hollow sphere fabricated of a plastic material has a plurality of holes extending there through. Deodorant in a spherical shape has a diameter less than the diameter of the hollow sphere. An intermediate support fabricated of plastic has a central section, an upper section, and a lower section. The central section being in a J-shaped cross sectional configuration. The upper section is an annular flange. The lower section is a circular upstanding edge with a diameter less than the diameter of the hollow sphere. The central section is formed with radial slots.

3 Claims, 2 Drawing Sheets

DEODORIZING SINK SYSTEM

RELATED APPLICATION

The present non-provisional application is based upon Provisional Application No. 62/020,477 Filed Jul. 3, 2014, the subject matter of which is incorporated herein by reference.

BACKGROUND OF THE INVENTION

Field of the Invention

The present invention relates to a deodorizing sink system and more particularly pertains to dissipating unpleasant odors in a kitchen sink and for creating a pleasant aroma throughout a kitchen, the dissipating and the creating being done in a safe, convenient, and economical manner.

SUMMARY OF THE INVENTION

In view of the foregoing disadvantages inherent in the known types of deodorizing sink system now present in the prior art, the present invention provides an improved deodorizing sink system. As such, the general purpose of the present invention, which will be described subsequently in greater detail, is to provide a new and improved deodorizing sink system and method which has all the advantages of the prior art and none of the disadvantages.

From a broad viewpoint, the present invention is a deodorizing sink system. A hollow sphere fabricated of a plastic material has a plurality of holes extending there through. Deodorant in a spherical shape has a diameter less than the diameter of the hollow sphere. An intermediate support fabricated of plastic has a central section, an upper section, and a lower section.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved deodorizing sink system which has all of the advantages of the prior art other and none of the disadvantages.

It is another object of the present invention to provide a new and improved deodorizing sink system which may be easily and efficiently manufactured and marketed.

It is a further object of the present invention to provide a new and improved deodorizing sink system which is of durable and reliable constructions.

An even further object of the present invention is to provide a new and improved deodorizing sink system which is susceptible of a low cost of manufacture with regard to both materials and labor, and which accordingly is then susceptible of low prices of sale to the consuming public, thereby making such deodorizing sink system economically available to the buying public.

Lastly, another object of the present invention is to provide a deodorizing sink system for dissipating unpleasant odors in a kitchen sink and for creating a pleasant aroma throughout a kitchen, the dissipating and the creating being done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
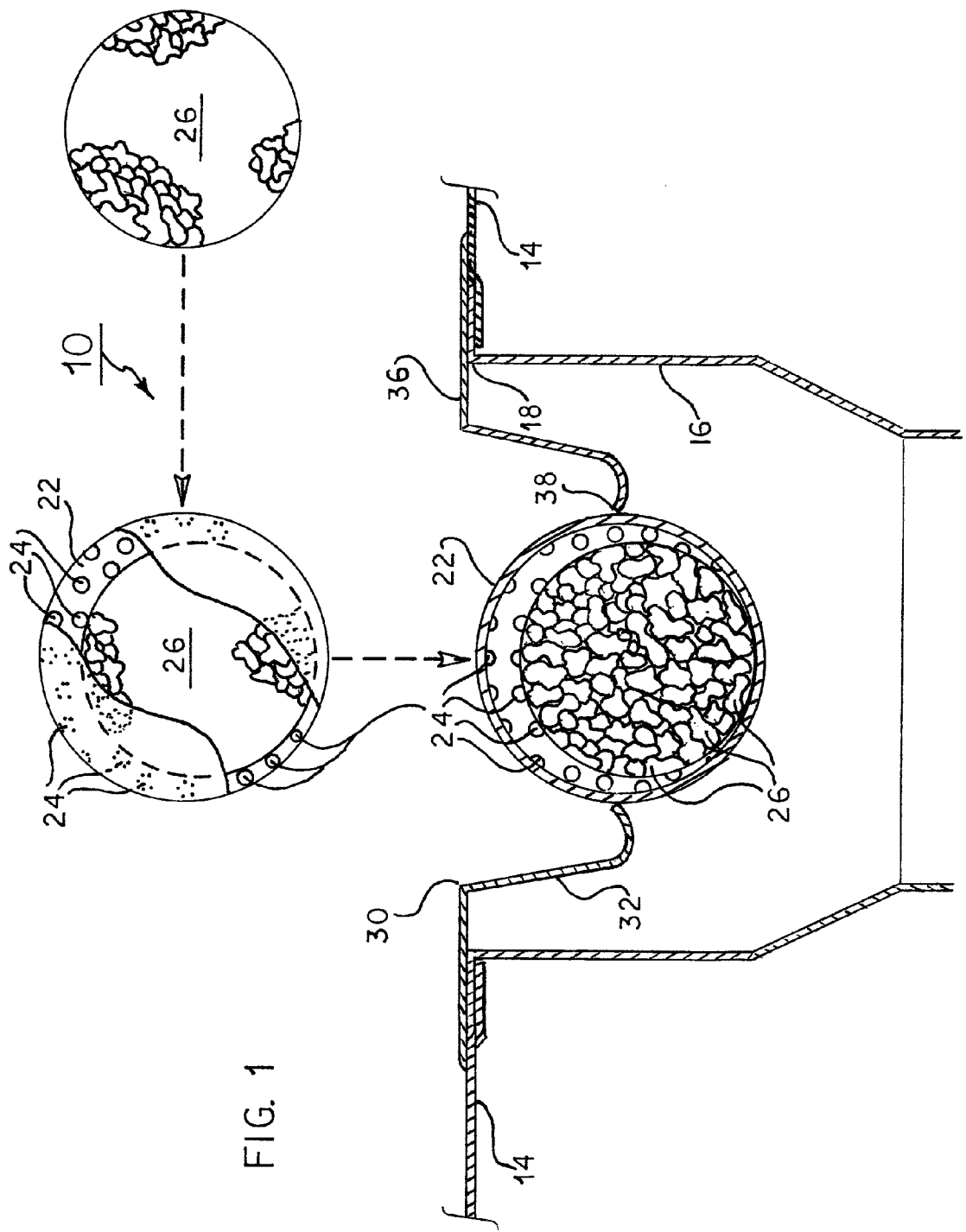
FIG. 1 is an exploded perspective illustration of a deodorizing sink system constructed in accordance with the principles of the present invention.
Figure 2:
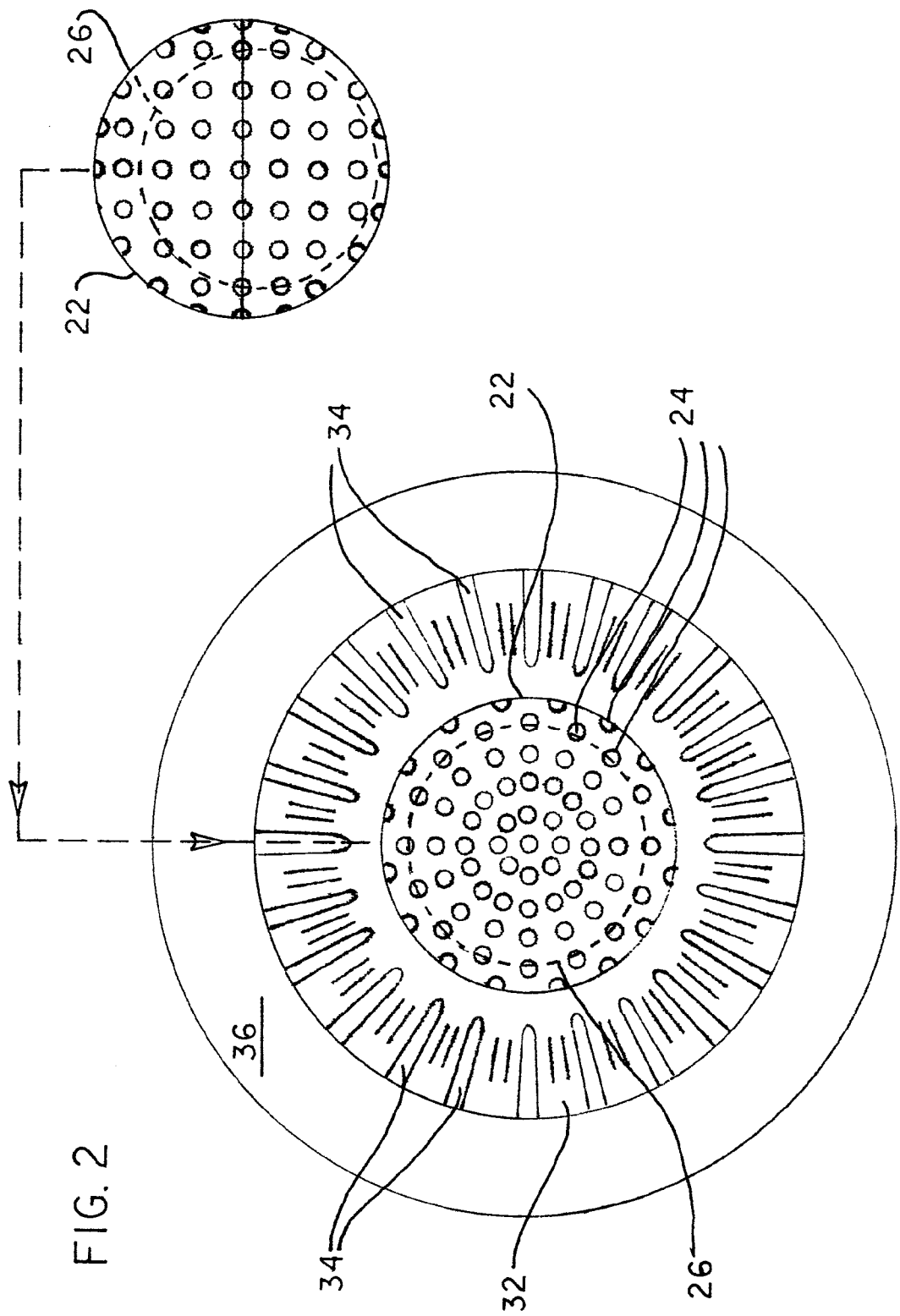
FIG. 2 is an exploded plan view of the deodorizing sink system of FIG. 1.

With reference now to the drawings, and in particular to FIG. 1 thereof, the preferred embodiment of the new and improved deodorizing sink system embodying the principles and concepts of the present invention and generally designated by the reference numeral 10 will be described.

The present invention, the deodorizing sink system 10 is comprised of a plurality of components. Such components in their broadest context include a hollow sphere and deodorant. Such components are individually configured and correlated with respect to each other so as to attain the desired objective.

From a specific viewpoint, the present invention is a deodorizing sink system 10. First provided is a kitchen sink 14. The kitchen sink has a horizontal upper surface. A circular aperture extends through the kitchen sink. Plumbing 16 is provided. The plumbing extends through the circular aperture. The plumbing has an upper end 18 adjacent to the circular aperture. The plumbing may or may not include a garbage disposal.

A hollow sphere 22 is provided. The hollow sphere has a diameter from 1.5 inches to 1.9 inches. A plurality of holes 24 extend through the hollow sphere. Each hole has a diameter of 0.125 inches plus or minus 10 percent with 90 to 100 holes formed entirely over the hollow sphere. The hollow sphere has two similarly configured hemispheres coupled together. The hollow sphere is fabricated of a plastic material. In an alternate embodiment of the invention, the hemispheres may be separably coupled as by screw threads.

Further provided is a deodorant 26 in a spherical shape. The deodorant has a diameter between 10 percent and 20 percent less than the diameter of the hollow sphere. The deodorant is located within the hollow sphere. The hollow sphere with the deodorant inside is, in the primary embodiment, a disposable commodity.

Provided last is an intermediate support 30. The intermediate support has a central section 32 with an upper section 36 and a lower section. The central section is in a J-shaped cross sectional configuration. The upper section is an annular flange supported upon the kitchen sink adjacent to the circular aperture. The lower section is a circular upstanding edge with a diameter between 0.125 inches and 0.250 inches less than the diameter of the hollow sphere. The upstanding edge supports the hollow sphere with holes above the upstanding edge and holes below the upstanding edge. The intermediate support is fabricated of plastic and is formed with radial slots 34. In this manner water falling into the kitchen sink will of necessity pass through the radial slots and the holes of the hollow sphere into contact with the deodorant, then out of the hollow sphere and through the plumbing.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A deodorizing sink system comprising:
a hollow sphere having a first diameter, a plurality of holes extending through the hollow sphere, each hole having a second diameter, the hollow sphere being fabricated of a plastic material;
a deodorant formed in a spherical shape, the deodorant having a third diameter less than the first diameter; and
an intermediate support having a central section and an upper section and a lower section, the central section being in a J-shaped cross sectional configuration, the upper section being an annular flange, the lower section being a circular upstanding edge with a diameter less than the diameter of the hollow sphere, the central section being formed with radial slots, the intermediate support being fabricated of plastic.

2. The system as set forth in claim 1 and further including a sink with plumbing, the intermediate support being supported in the plumbing whereby water falling into the kitchen sink will of necessity pass through the holes of the hollow sphere into contact with the deodorant then out of the hollow sphere and through the plumbing.

3. A deodorizing sink system (10) for dissipating unpleasant odors in a kitchen sink and for creating a pleasant aroma throughout a kitchen, the dissipating and the creating being done in a safe, convenient, and economical manner, the system comprising:
a kitchen sink (14) having a horizontal upper surface and a circular aperture extending through the kitchen sink, plumbing (16) extending through the circular aperture, the plumbing having an upper end (18) adjacent to the circular aperture;
a hollow sphere (22), the hollow sphere having a diameter from 1.5 inches to 1.9 inches, a plurality of holes (24) extending through the hollow sphere, each hole having a diameter of 0.125 inches plus or minus 10 percent with from 90 to 100 holes formed entirely over the hollow sphere, the hollow sphere being formed of two similarly configured hemispheres coupled together, the hollow sphere being fabricated of a plastic material;
a deodorant (26) formed in a spherical shape, the deodorant having a diameter between 10 percent and 20 percent less than the diameter of the hollow sphere, the deodorant being located within the hollow sphere;
an intermediate support (30), the intermediate support having a central section (32) with an upper section section (36) and a lower section, the central section being in a J-shaped cross sectional configuration, the upper section being an annular flange supported upon the kitchen sink adjacent to the circular aperture, the lower section being a circular upstanding edge with a diameter between 0.125 inches and 0.250 inches less than the diameter of the hollow sphere, the upstanding edge supporting the hollow sphere with holes above the upstanding edge and with holes below the upstanding edge, the intermediate support being fabricated of plastic and formed with radial slots (34) whereby water falling into the kitchen sink will of necessity pass through the radial slots and the holes of the hollow sphere into contact with the deodorant then out of the hollow sphere and through the plumbing.

* * * * *